US006402933B1

(12) United States Patent
Dowling

(10) Patent No.: US 6,402,933 B1
(45) Date of Patent: Jun. 11, 2002

(54) METHOD AND SYSTEM OF PREVENTING CORROSION OF CONDUCTIVE STRUCTURES

(75) Inventor: David B. Dowling, New York, NY (US)

(73) Assignee: Applied Semiconductor, Inc., New York, NY (US)

( * ) Notice: Subject to any disclaimer, the term of this patent is extended or adjusted under 35 U.S.C. 154(b) by 0 days.

(21) Appl. No.: 09/875,992

(22) Filed: Jun. 8, 2001

(51) Int. Cl.[7] .................................................. C23F 13/06
(52) U.S. Cl. ........................ 205/725; 205/731; 205/734; 205/735; 205/740; 204/196.12; 204/196.16; 204/196.37
(58) Field of Search .................................. 205/724, 725, 205/731, 734, 735, 740; 204/196.12, 196.16, 196.37

(56) References Cited

U.S. PATENT DOCUMENTS 6,325,915 B1 * 12/2001 Dowling et al. ............ 205/724

OTHER PUBLICATIONS

U.S. application No. 09/585,397, filed Jun. 2, 2000, allowed.

* cited by examiner

*Primary Examiner*—Bruce F. Bell
(74) *Attorney, Agent, or Firm*—Oblon, Spivak, McClelland, Maier & Neustadt, P.C.

(57) ABSTRACT

A system for preventing corrosion of a surface of a metal structure in contact with a corrosive environment comprising:
 (a) a semiconductive organic polymer coating in conductive contact with at least part of the surface; and
 (b) an electronic filter for filtering corrosive noise
and a method of preventing corrosion using the system.

35 Claims, 2 Drawing Sheets

METHOD AND SYSTEM OF PREVENTING CORROSION OF CONDUCTIVE STRUCTURES

BACKGROUND OF THE INVENTION

1. Field of the Invention

The present invention relates to a method and system for the prevention of corrosion of conductive structures combining organic coatings and semiconductor technology.

2. Discussion of the Background Art

A variety of methods for controlling corrosion have evolved over the past several centuries, with particular emphasis on methods to extend the life of metallic structures in corrosive environments. These methods typically include protective coatings which are used principally to upgrade the corrosion resistance of ferrous metals, such as steel, and some nonferrous metals, such as aluminum, and to avoid the necessity for using more costly alloys. Thus, they both improve performance and reduce costs. However, such protective coatings typically have several pitfalls, including poor applicability to non-metallic structures that suffer from corrosion or fouling.

Protective coatings fall into two main categories. The largest of these categories is the topical coating such as a paint, that acts as a physical barrier against the environment. The second category consists of sacrificial coatings, such as zinc or cadmium, that are designed to preferentially corrode in order to save the base metal from attack.

Cathodic protection and coatings are both engineering disciplines with a primary purpose of mitigating and preventing corrosion. Each process is different: cathodic protection prevents corrosion by introducing an electrical current from external sources to counteract the normal electrical chemical corrosion reactions whereas coatings form a barrier to prevent the flow of corrosion current or electrons between the naturally occurring anodes and cathodes or within galvanic couples. Each of these processes provided limited success. Coatings by far represent the most widespread method of general corrosion prevention (see Leon et al U.S. Pat. No. 3,562,124 and Hayashi et al U.S. Pat. No. 4,219,358). Cathodic protection, however, has been used to protect hundreds of thousands of miles of pipe and acres of steel surfaces subject to buried or immersion conditions.

The technique of cathodic protection is used to reduce the corrosion of the metal surface by providing it with enough cathodic current to make its anodic dissolution rate become negligible (for examples, see Pryor, U.S. Pat. No. 3,574,801; Wasson U.S. Pat. No. 3,864,234; Maes U.S. Pat. No. 4,381,981; Wilson et al U.S. Pat. No. 4,836,768; Webster U.S. Pat. No. 4,863,578; and Stewart et al U.S. Pat. No. 4,957,612). The cathodic protection concept operates by extinguishing the potential difference between the local anodic and cathodic surfaces through the application of sufficient current to polarize the cathodes to the potential of the anodes. In other words, the effect of applying cathodic currents is to reduce the area that continues to act as an anode, rather than reduce the rate of corrosion of such remaining anodes. Complete protection is achieved when all of the anodes have been extinguished. From an electrochemical standpoint, this indicates that sufficient electrons have been supplied to the metal to be protected, so that any tendency for the metal to ionize or go into solution has been neutralized.

Recent work in the study of corrosion has found that electrochemical corrosion processes appear to be associated with random fluctuations in the electrical properties of electrochemical systems, such as cell current and electrode potential. These random fluctuations are known in the art as "noise". Researchers have begun to apply noise analysis techniques to study the processes of corrosion in electrochemical systems.

Riffe, U.S. Pat. No. 5,352,342 and Riffe U.S. Pat. No. 5,009,757 disclose a zinc/zinc oxide based silicate coating that is used in combination with electronics in a corrosion prevention system. The zinc/zinc oxide particles in the coating are disclosed as having semiconductor properties, primarily a p-n junction at the Zn—ZnO phase boundary. When reverse biased, this p-n junction is described as behaving as a diode and inhibiting electron transfer across the boundary. This restriction limits electron transfer from sites of Zn oxidation to the sites of oxygen reduction on the ZnO surface. Effectively, there is increased resistance between the anode and cathode of local corrosion cells and corrosion is reduced.

On average, the Zn—ZnO based junction will be reversely biased due to the potentials associated with the oxidation of Zn at the Zn surface and the reduction of $O_2$ at the ZnO surface. However, significant stochastic voltage fluctuations occur. These voltage fluctuations cause the junction to episodically become forward biased. When forward biased, electron transfer across the junction increases and there is an acceleration of the oxidation of Zn and reduction of $O_2$. Effectively, there is a short circuit between the anode and cathode of local corrosion cells and corrosion is enhanced.

The Riffe patents disclose attachment of a fixed value capacitor in the electrochemical circuit of the corrosion prevention system. However, there is no way to control the level of capacitance nor any method suggested for determining the level of capacitance needed to effectively prevent corrosion in any given structure. Hence, it is necessary to use an overcapacitance in the system to be effective.

Recently, the development of conductive organic polymers has reached the point where they are commercially feasible. Their uses range from charge-storage batteries, antistatic films, conductive hosings, gaskets, cable shields, conductive textiles, chemical sensors, electromagnetic shielding, gas separation membranes, electrooptic devices, discharge layers in electrolithographic applications, and as corrosion-preventive paints. One such corrosion preventive application is a commercial product known as CATIZE, available from GeoTech Chemical Company, LLC through its distributor Seegott, Inc. of Ohio. This is a conductive polyaniline polymer doped with zinc metal or ions, which is used as a sacrificial cathodic protective layer on metal structures.

One drawback to previous corrosion preventive methods, such as that of Riffe disclosed above, is the relative inflexibility of color selection available for the silicate based coatings disclosed therein, with the only color readily available being grey. While this is acceptable in most marine and structural uses, there is a need for corrosion preventive coatings that are non-sacrificial and which can be provided in a range of colors for use as paint substitutes, particularly in the automotive and transportation industries.

SUMMARY OF THE INVENTION

Accordingly, one object of the present invention is to provide an organic conductive polymer coating that provides anticorrosion properties to any conductive structure.

A further object of the present invention is to provide a method for protecting conductive metallic structures from corrosion that is fine-tuned to the unique characteristics of the metallic structure.

A further object of the present invention is to provide a method for preventing corrosion of conductive structures by using organic polymer based semiconductor technology and with no external anode, no electrolyte, and no current flow.

A further object of the present invention is to provide a system for protecting conductive structures from corrosion, wherein the system provides long term protection with minimal system maintenance required.

A further object of the present invention is to provide an organic polymer coating having anti-corrosion properties and which can be provided in any desired color for use as a paint substitute.

These and other objects have been satisfied by the discovery of a semiconductive organic polymer coating and associated electronic system, wherein the system can be operated by merely filtering voltage fluctuations in the conductive structure on which the semiconductive organic coating is placed, wherein the method for using the system comprises:

coating the conductive structure with a semiconductive organic polymer coating with a fixed electronic filter connected to said coated structure, monitoring noise generated by said coating having said fixed electronic filter connected thereto, using an adjustable filter connected to said coating to determine an anti-corrosive filter response needed to minimize the noise generated by said coating; and replacing said adjustable filter with a passive or active filter having a filter response of at least said anti-corrosive filter response.

BRIEF DESCRIPTION OF THE FIGURES

A more complete appreciation of the invention and many of the attendant advantages thereof will be readily obtained as the same become better understood by reference to the following detailed description when considered in connection with the accompanying Figures, wherein.

DETAILED DESCRIPTION OF THE PREFERRED EMBODIMENTS

Figure 1:
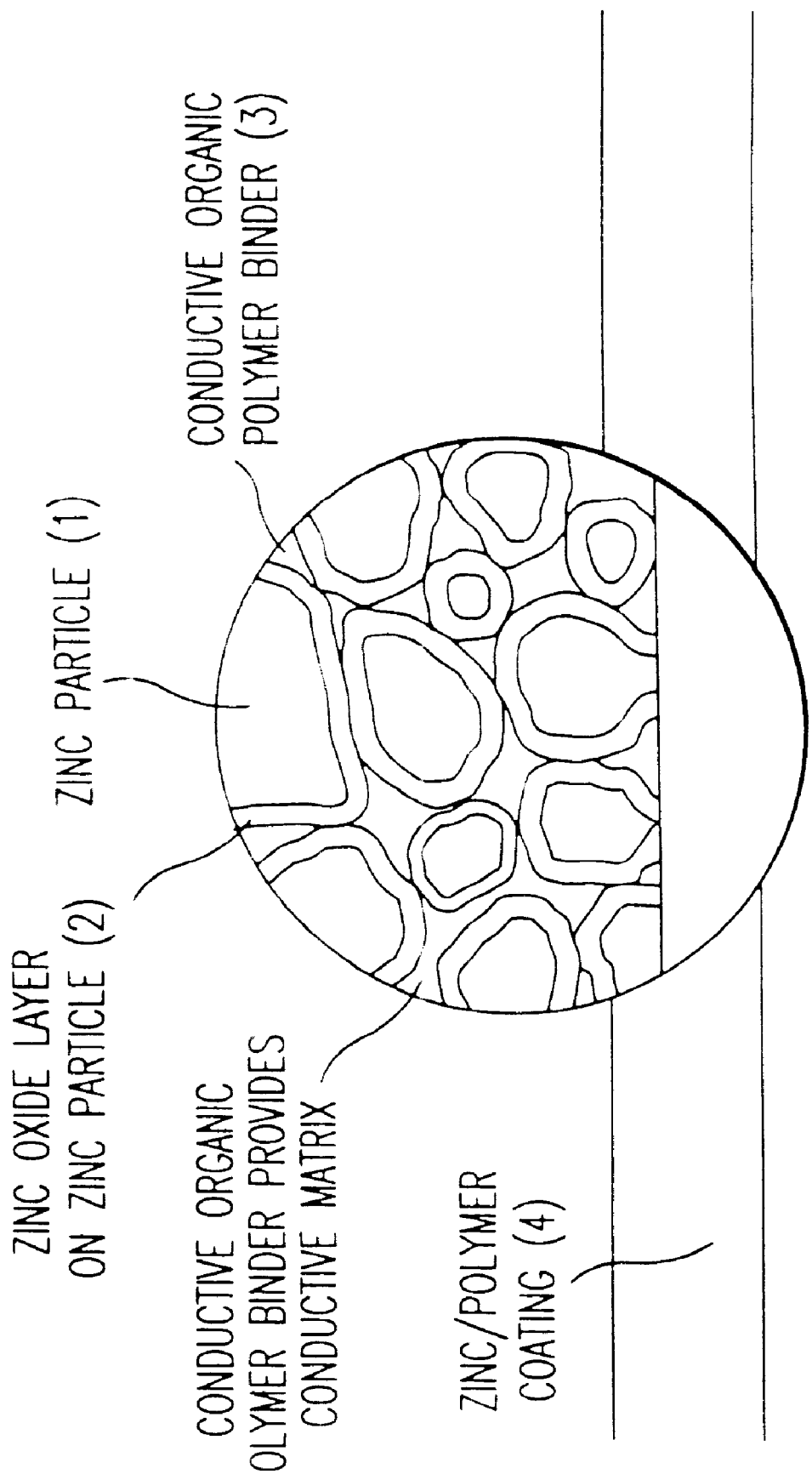
FIG. 1 is a graphical representation of the Zn/ZnO junction of a preferred embodiment of the present invention.

The present invention provides a method for the prevention of corrosion for any conductive structure susceptible to corrosion comprising coating the conductive structure with a semiconductive organic polymer coating and connecting the resulting coated structure to a fixed electronic filter, monitoring the corrosive noise generated by the system, and determining the filter response needed to minimize the corrosive noise (within the context of the present invention, the term "corrosive noise" is used to describe the voltage fluctuations that occur due to the galvanic corrosion process). In one embodiment the present invention comprises adjusting the filter response using an adjustable filter to determine the filter response needed to minimize the noise generated by the coated structure, then replacing the adjustable filter with a passive electronic filter having at least the determined anti-corrosive filter response. In an alternative embodiment, the invention replaces the adjustable filter with an active electronic filter and monitoring system that continuously monitors the noise and automatically adjusts the filter response to minimize the fluctuations in the system.

The present invention minimizes this corrosive noise by coupling the semiconductive organic polymer coating to an electronic filter. The electronic filter has a filter response, defined within the context of the present invention as the level of reduction of noise at a given frequency. As noted above, the filter can be a passive, low-pass RC filter or an active filter. In each case, the filter minimizes the voltage fluctuations. The junctions present in the semiconductor coating then maintain a reverse bias. The time-averaged electron flow from the anodic to the cathodic domains in the semiconductive organic polymer coating is then reduced and the coating is effectively passivated.

A passive, low-pass RC filter is essentially a capacitor and a resistor. In the case of the present system, the semiconductive organic polymer coating is believed to act somewhat as the resistor, with a capacitor completing the RC filter. Suitable active filters include, but are not limited to, Butterworth filters, Bessel filters, and Sallen-Key filters. These active filters are commercially available and/or can be readily prepared by those of ordinary skill in the art. These active filters are basically an op-amp circuit with capacitors. Preferably, a main component of the filters of the present invention is a capacitor, wherein the filter response is related to the capacitance needed to provide the reduction of noise at the given frequency.

The noise measurement aspects of the present invention are used to fine-tune the design of the system for specific applications. Based on the measured noise, the requisite filter properties and location of filter installation in the system can be determined and improved for consistent corrosion prevention over the entire surface of the structure, even in very large structures, such as aircraft carriers or large span bridges. In the present invention, the voltage fluctuations between the coated surface and a low-noise, high impedance reference electrode are monitored. A suitable high impedance reference electrode can be prepared from a saturated calomel electrode or a saturated sulfate electrode, for example. A commercially available high impedance reference electrode suitable for this purpose can be obtained from various catalog equipment companies, such as Beckman Instruments or Corning. The noise can be monitored using these electrodes by use of an oscilloscope to show the voltage fluctuations. Alternatively, the data obtained from the electrodes can be stored and analyzed using a PC computer with an analog-digital converter, and analyzing the resulting data using time series analysis programs, such as fast Fourier transform (FFT) analysis or a maximum entropy method (MEM method). These methods can provide both real-time and delayed results, as desired. Using such methods permits determination of the level of filter response and placement of the filters needed to generate a nearly flat line on the oscilloscope (i.e. minimize the noise). This can be done at a single location of the structure, or for finer control, at a plurality of locations around the structure surface. The electronic filter properties and filter installation locations can be adjusted to minimize the measured voltage fluctuations, thus maximizing the passivation of the coating. The ultimate result is a dramatic increase in the lifetime of the corrosion prevention system for any desired structure type. This occurs due to the reduction of the corrosive noise, thus drastically reducing the sacrificial corrosion of the semiconductive organic polymer coating.

The present invention also relates to a semiconductive organic polymer coating that can be used with a variety of conductive substrates to provide an array of interesting properties. The semiconductive organic polymer coating of the present invention can be any conductive or semiconductive organic polymer coating, including but not limited to, polyacetylenes, polyphenylenes, polyfurans, polythiophenes, polypyrroles, poly(arylene vinylenes), and polyanilines, in doped or undoped form. Further, the organic polymer coating of the present invention can be a blend, composite or colloid of any of these polymer types with any suitable thermoplastic or thermoset polymer, and optionally with one or more conventional fillers, such as fiberglass, mineral fillers, carbon fibers, etc. Various electroconductive organic polymers are disclosed in Kirk-Othmer Encyclopedia of Chemical Technology, 4$^{th}$ Ed., Volume 9, pages 61–85 (1994), the entire contents of which are incorporated herein by reference. The coating can be further formulated as a colored coating using one or more dyes or pigments conventionally used in the coatings or paint industry, so long as the dye or pigment does not disrupt the electroconductivity of the organic polymer coating. Preferred coatings include CATIZE (a combination of polyaniline and zinc metal, as noted above), BAYTRON P (a PEDT/PSS [poly(3,4-ethylenedioxythiophene) poly(styrene sulfonate)] polymer that is intrinsically conductive, transparent, and virtually colorless (pale blue)) and LIGNO-PANI (a polyaniline), all commercially available from Geotech Chemical Co., LLC, through its distributor Seetech, Inc. of Ohio.

The semiconductive organic polymer coating of the present invention can be used in a variety of end uses. Chief among these end-uses is the prevention of corrosion of conductive structures. The present system for preventing corrosion of conductive substrates comprises:

(a) a semiconductor organic polymer coating in conductive contact with at least part of the surface of the conductive structure; and (b) means for filtering corrosive noise, wherein the means comprise an electron sink, such as a battery or other power supply, along with a filter, such as a capacitor, connected to the coated conductive substrate and the discovery of a corrosion prevention method comprising:

1) cleaning the external surface of a conductive structure;

2) coating the external surface with the semiconductive organic polymer coating of the present invention; and 3) using an electronic filter to minimize corrosive noise in the system.

The key to the method and system of the present invention is the measurement of corrosive noise generated by the entire system (including, but not limited to, the substrate, coating and filter components) and minimizing that noise by application of an electronic filter.

In the embodiment for corrosion and fouling prevention, the present system comprises two interdependent components: (1) the semiconductive organic polymer coating, and (2) a means for imparting a net negative bias to the conductive structure to which the coating is applied. In general the semiconductive organic polymer coating is applied to the conductive surface after it has been cleaned, preferably by grit blasting to a commercial blast finish for metal surfaces or a comparable process for non-metallic conductive structures. When a conductive surface is cleaned by grit blasting or comparable methods, the surface will have numerous grooves or indentations of from 0.1 mil up to several mil in depth. The semiconductive organic polymer coating of the present invention should be applied at a depth of at least 2 mil greater than the depth of the pits formed from the cleaning process, preferably from 2 to 10 mil thickness, most preferably 7 to 9 mil thick. On smooth surfaces without significant pits, the coating can be applied at thicknesses down to about 0.5 mil without detrimentally affecting the system performance.

The structure that can be protected using the present method and system can be any conductive material susceptible to corrosion. Preferably the structure is a metallic structure of a ferrous metal or non-ferrous conductive metal. Typical metals include, but are not limited to, iron, steel, and aluminum. In a most preferred embodiment the substrate is the metal body of an automobile or other vehicle and the semiconductive organic polymer coating comprises the organic conductive polymer (optionally containing a conductive dopant, such as Zn) and one or more dyes or pigments to provide a color of coating as desired. In this embodiment, the automotive body can be provided with the desired color in a single coating application, with anti-corrosion properties, a considerable improvement over the multiple (typically combination of 3 or more primer, color and topcoat layers total) coating applications required in conventional automotive operations. In a more preferred embodiment, the entire metal bodywork of the automobile is coated on all exposed surfaces using a single dip coating in the semiconductive organic polymer coating of the present invention, with the electronic monitoring and filtering apparatus of the system being applied after final assembly of the automobile.

The semiconductive organic polymer coating of the present invention preferably comprises (a) a conductive-organic polymer, with or without dopant, and, (b) optionally, one or more metals or metal alloys, with or without the presence of the oxide(s) of the metal(s). In a most preferred embodiment, the metal or metal alloy contained within the coating is a Zn/ZnO system. The conductive organic polymer, or the metal or metal alloy in the coating (when present), must have a higher oxidation potential than the conductive material to be protected. Most preferably, due to the oxidation potential of most materials to be protected, the semiconductive organic polymer coating of the present invention contains one or more metals or metal alloys, with or without the presence of the oxide of the metal. Standard electrode potentials for most metals are well known and are reproduced below for a variety of different metals.

Standard Electrode Reduction Potentials (Relative to Hydrogen Electrode)

$Fe^{+2}+2e-\ Fe: -0.41$ $Zn^{+2}+2e-\ Zn: -0.76$ $Ti^{+2}+2e-\ Ti: -1.63$ $Al^{+3}+3e-\ Al: -1.71$ $Ce^{+3}+3e-\ Ce: -2.34$ $Mg^{+2}+2e-\ Mg: -2.38$ $Ba^{+2}+2e-\ Ba: -2.90$ $Cs^{+}+e-\ Cs: -2.92$ (Source: CRC Handbook of Chemistry and Physics, 60$^{th}$ ed., Ed. Robert C. Weast, CRC Press, Inc, Boca Raton, Fla., 1979)

Because the coating of the present system and method is sacrificial with respect to the conductive material being protected (although minimally sacrificial when the corrosive noise has been minimized), when determining the metal to be contained in the coating, it is important to select a metal having a standard electrode potential that is more negative than the conductive material to be protected. For example, to protect Fe (such as present in steel), the coating can use Zn, Ti or any of the other metals having a standard electrode potential more negative than −0.44. When protecting a metal having a very negative electrode potential, such as aluminum (−1.68), it is acceptable to use an alloy of a metal having a less negative electrode potential (such as Zn) combined with a metal having a more negative electrode potential (such as Mg). This alloy will provide the coating with the requisite sacrificial nature while avoiding the extreme oxidation that would occur with a coating containing only the highly negative electrode potential metal such as Mg. It is also possible to avoid a coating that is too quickly sacrificial by incorporating the highly negative electrode potential metal into one of the above noted binders. Instead of an alloy of two metals, the more negative electrode potential metal can be incorporated as the counterion of the silicate binder.

The coating of the present invention can also include additional n-type semiconductors incorporated into the coating, such as Sn/SnO. In addition, the coating can be doped with metals such as Al or Ga to increase the conductivity of the coating or 1–5% of Li to reduce the conductivity of the coating. The metal/metal oxide interface (Zn/ZnO) in the preferred coating of the present invention acts as a diode in the electrochemical system. Thus, the coating contains many microdomains acting as diodes. Because of the corrosive noise generated by the coating, the diode periodically switches on and off due to fluctuations in the conductive potential of microdomains in the coating. This fluctuation of the conductive potential and switching of the diode causes the coating to corrode sacrificially. By reducing the conductivity of the coating by doping, such as with Li, it is possible to lower the switching potential of the diode to below the lowest point in the noise fluctuation curve. This will minimize the sacrificial corrosion of the coating, while still protecting the conductive material of the structure to be protected.

It may be added that by properly selecting the semiconductor organic polymer coating material for a conductive surface, one can realize both the traditional passive as well as the novel active barriers.

In a preferred embodiment, the zinc dust of the coating of the present invention forms a metal-semiconductor junction where the zinc metal and zinc oxide interface, with the zinc oxide being an n-type semiconductor.

A preferred embodiment of the completed coating is schematically shown in FIG. 1. FIG. 1 shows the porous nature of the preferred zinc/zinc oxide/polymer coating (4) of the present invention. The zinc particles (1) are covered by a zinc oxide layer (2) with the various oxide coated particles surrounded by a conductive organic polymer binder (3).

The conductive structure of the present invention can be any conductive structure in need of protection from corrosion, including both metal structures and non-metal structures. Examples of such metal structures include metal vehicles, such as ships, planes, automobiles, military tanks or transports, metal vehicle parts, bridges, railroad coupling mechanisms, containers, pipes and metal towers, as well as smaller structures such as biomedical devices. Examples of metal vehicle parts include metal parts of vehicles such as automobiles, airplanes, trains, military land vehicles such as tanks, and ships and other marine vehicles. Examples of containers are refinery containers, storage silos and storage bins. Examples of non-metal conductive structures include conductive concrete and conductive polymeric structures. Corrosive processes also affect these non-metal conductive structures and can also be minimized by the present invention. Conductive concrete has been proposed as a possible material for preparation of floating airport runways. The system of the present invention would help prevent corrosion of the concrete, thus extending the life and structural integrity of the concrete structures.

One significant advantage obtained in the present invention is that by minimizing the sacrificial corrosion of the semiconductive organic polymer coating, the life of the coating will be extended to be many times longer than that of conventional coating protection systems. While this would be possible to achieve under water through the application of cathodic current, it would require substantial current and would be very difficult to control. The method of the present invention functions internally to the coating and thus prevents atmospheric corrosion where the corroding medium is nothing more than moisture condensed from the air. This becomes extremely important in protecting such surfaces as the bodywork of automobiles and other vehicles, as well as the internal surfaces of modern ships, where designs to provide increased strengths have concomitantly increased corrosion prone areas, as well as in protecting automobile parts, bridges, airplanes, and trains.

Another preferred embodiment is the use of the present method and system on the internal surfaces of modem ships where the condensation is most corrosive due to its high saline content and where, at the same time, there is insufficient moisture for cathodic protection systems to function. Without the noise filter of the present invention, the zinc in the coating would quickly leach out and be eroded away by the flow of condensate to the bilges. However, upon the application of a noise filter in accordance with the present invention to the metallic substrate, this leaching is effectively halted.

Additionally, the use of a noise filter on the substrate steel of the automobile provides substantially no interference to onboard electronics, an important consideration in the highly computerized and electronic automobiles currently marketed. Further, its use on the substrate steel of a ship provide no greater interference than turning on a light bulb within the ship, nor would it yield a detectable signal to hostile detection devices, since the noise filter, even those that use a battery or other source of electrons, does not produce a field that would radiate perceptibly beyond the coating. The absorbance characteristics of zinc are well known and are often used for EM shielding and electronics enclosures. Thus, there would also be no measurable EM radiation from shore-based structures to which the present system is applied.

The fixed electronic filter of the present invention acts as a capacitor having an electron sink attached thereto to keep the capacitor reverse biased. The fixed electronic filter is preferably a combination of a conventional power supply, for example a direct current (DC) power supply means such as a battery, preferably a 12 Volt battery, and solar cells and alternating current (AC) power supply means. It is to be noted that although this component is termed a "power supply" in the present description, there is no current and no voltage in the present system. Accordingly, the power supply nomenclature is merely for convenience and is not intended to imply electron flow. The power supply means used preferably would be sufficient to deliver a voltage of from 0.5 to 30 V, most preferably 10 to 20 V, if a completed circuit were available. The fixed electronic filter (i.e., power supply and capacitor) can be connected to the coated conductive substrate, either directly to the substrate or to the coating. In a preferred embodiment, the power supply means of the present invention has a negative terminal directly coupled to the conductive structure to be protected. The positive terminal of the power supply means is coupled to the conductive structure by way of the filter/capacitor, to a portion of the structure remote from the negative terminal connection. With the use of a conductive organic polymer as the coating of the present invention, these electrical connections can instead be made directly to the organic polymer coating, rather than the conductive structure, or the positive terminal can be connected to one of the organic polymer coating or the conductive structure with the negative terminal connection being made to the other. Since the present invention does not rely on creation of current flow, which drops off as the distance between terminals increases, the distance between the terminals is not critical, so long as the positive and negative terminals do not touch one another. The positive terminal connection is preferably made to a location on the structure from 0.01 meter to 30 meters from the location of the negative terminal connection, most preferably from 5 to 10 meters from the location of the negative terminal connection.

The method of the present invention is self-tending for the life of the system. There are no currents or potentials to monitor and control periodically as there would be in a conventional cathodic protection system. Further, there is no possibility that the present system can go out of control and severely damage the supporting structures as can occur in an impressed cathodic protection system. The only effective reduction in the life of the coating would therefore come from wind and water-borne abrasion. Since the abrasion resistance of the coating is somewhat better than that of galvanize, the life expectancy of the coating can be extended to the range of several decades.

Additionally, with the use of an active filter and monitoring system that continually monitors noise fluctuations and adjusts the filter properties, such as filter response and cutoff frequency, the coating lifetime can be extended by preventing increases in the rate of sacrificial loss due to increases in corrosion over time.

Figure 2:
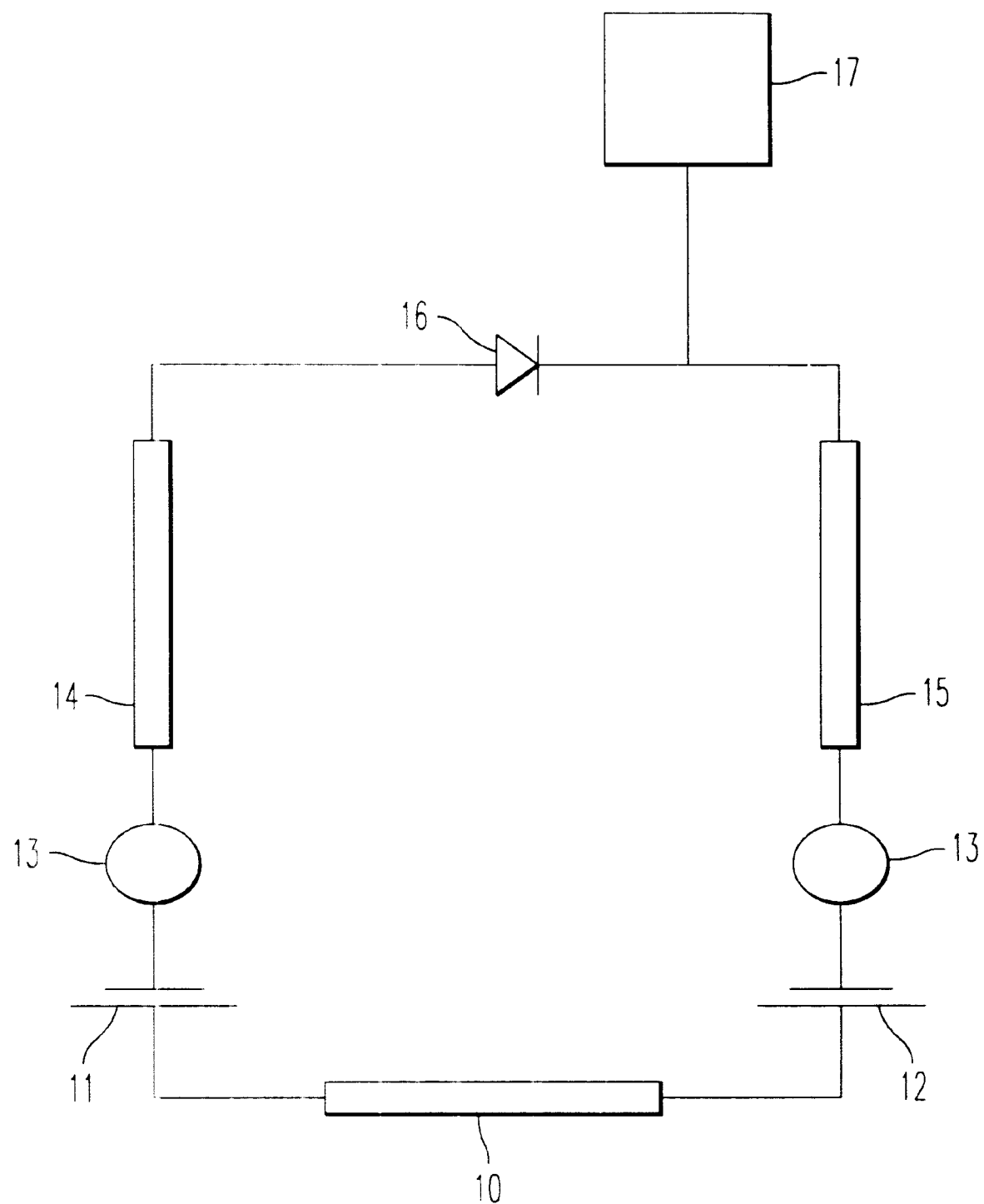
FIG. 2 shows an equivalent circuit diagram depicting the system of the present invention.

FIG. 2 shows an equivalent circuit diagram depicting the system of the present invention. In the circuit, 10 is the Solution resistance (Rs), with 11 and 12 being the galvanic electrode potential at the anode (Ea) and cathode (Ec), respectively. The noise source (En) in the circuit is represented by 13. The faradaic impedance of the anode (Ra) and cathode (Rc) are shown in 14 and 15, respectively. The metal-semiconductor junction at the Zn/ZnO boundary is shown as diode (D) 16. The noise filter (F), whether active or passive filter, is represented by 17.

Obviously, numerous modifications and variations of the present invention are possible in light of the above teachings. It is therefore to be understood that within the scope of the appended claims, the invention may be practiced otherwise than as specifically described herein.

What is claimed is:

1. A method for preventing corrosion of a conductive structure in contact with a corrosive environment, said method comprising:
   (a) coating the conductive structure with a semiconductive organic polymer coating and providing an electronic filter connected to the coated conductive structure;
   (b) monitoring corrosive noise generated by the coated conductive structure and adjusting filter properties of said electronic filter to minimize the corrosive noise.

2. The method of claim 1, wherein said electronic filter comprises a power source and a capacitor.

3. The method of claim 1, wherein said monitoring and adjusting step (b) is performed continually using an active filter and monitoring means.

4. The method of claim 1, wherein said electronic filter comprises a plurality of capacitors and said step (b) further comprises determining a placement of each of said plurality of capacitors on said conductive structure.

5. The method of claim 1, wherein said conductive structure is a metal conductive structure.

6. The method of claim 5, wherein said metal conductive structure comprises a metal selected from the group consisting of ferrous metals and conductive non-ferrous metals.

7. The method of claim 6, wherein said metal is steel.

8. The method of claim 6, wherein said metal is aluminum.

9. The method of claim 1, wherein said conductive structure is selected from the group consisting of bridge members, railroad coupling mechanisms, refineries, containers, metal towers, and conductive concrete structures.

10. The method of claim 1, wherein said conductive structure is selected from the group consisting of automobiles, automobile parts, trucks, buses and construction equipment.

11. The method of claim 1, wherein said semiconductive organic polymer coating comprises a conductive organic polymer and one or more metals, metal alloys or non-metal semiconductor materials.

12. The method of claim 11, wherein said conductive organic polymer is a member selected from the group consisting of polyacetylenes, polyphenylenes, polyfurans, polythiophenes, polypyrroles, poly(arylene vinylenes), polyanilines, and doped compositions thereof.

13. The method of claim 11, wherein said one or more metals or metal alloys comprises a metal selected from the group consisting of Zn, Ti, Al, Ga, Ce, Mg, Ba, Cs, the corresponding metal oxides and alloys thereof.

14. The method of claim 13, wherein said one or more metals or metal alloys comprises a mixture of one or more metals selected from the group consisting of Zn, Ti, Al, Ga, Ce, Mg, Ba and Cs and one or more metal oxides obtained therefrom.

15. The method of claim 13, wherein said one or more metals or metal alloys is a combination of zinc/zinc oxide.

16. The method of claim 1, wherein said semiconductive organic polymer coating further comprises one or more dyes or pigments.

17. A system for preventing corrosion of a conductive structure, comprising:
   (a) a semiconductive organic polymer coating;
   (b) a fixed electronic filter;
   (c) a corrosive noise monitoring system; and
   (d) an adjustable filter.

18. The system of claim 17, wherein said corrosive noise monitoring system further comprises a high impedance reference electrode and an oscilloscope.

19. The system of claim 17, wherein said adjustable filter is selected from the group consisting of manually adjustable filters and active filters.

20. The system of claim 17, wherein said semiconductive organic polymer coating comprises a conductive organic polymer and one or more metals, metal alloys or non-metal semiconductor materials.

21. The system of claim 20, wherein said conductive organic polymer is a member selected from the group consisting of polyacetylenes, polyphenylenes, polyfurans, polythiophenes, polypyrroles, poly(arylene vinylenes), polyanilines, and doped compositions thereof.

22. The system of claim 20, wherein said one or more metals or metal alloys comprises a metal selected from the group consisting of Zn, Ti, Al, Ga, Ce, Mg, Ba, Cs, the corresponding metal oxides and alloys thereof.

23. The system of claim 22, wherein said one or more metals or metal alloys comprises a mixture of one or more metals selected from the group consisting of Zn, Ti, Al, Ga, Ce, Mg, Ba and Cs and one or more metal oxides obtained therefrom.

24. The system of claim 22, wherein said one or more metals or metal alloys is a combination of zinc/zinc oxide.

25. The system of claim 17, wherein said semiconductive organic polymer coating further comprises one or more dyes or pigments.

26. A corrosion protected vehicle, comprising:
    a vehicle having one or more metal exterior parts, wherein at least one of said one or more metal exterior parts is coated with a layer of a semiconductive organic polymer coating;
    a corrosive noise monitoring system; and
    an adjustable filter.

27. The vehicle of claim 26, wherein said corrosive noise monitoring system further comprises a high impedance reference electrode and an oscilloscope.

28. The vehicle of claim 26, wherein said adjustable filter is an active filter.

29. The vehicle of claim 26, wherein said semiconductive organic polymer coating comprises a conductive organic polymer and one or more metals, metal alloys or non-metal semiconductor materials.

30. The vehicle of claim 29, wherein said conductive organic polymer is a member selected from the group consisting of polyacetylenes, polyphenylenes, polyfurans, polythiophenes, polypyrroles, poly(arylene vinylenes), polyanilines, and doped compositions thereof.

31. The vehicle of claim 29, wherein said one or more metals or metal alloys comprises a metal selected from the group consisting of Zn, Ti, Al, Ga, Ce, Mg, Ba, Cs, the corresponding metal oxides and alloys thereof.

32. The vehicle of claim 31, wherein said one or more metals or metal alloys comprises a mixture of one or more metals selected from the group consisting of Zn, Ti, Al, Ga, Ce, Mg, Ba and Cs and one or more metal oxides obtained therefrom.

33. The vehicle of claim 31, wherein said one or more metals or metal alloys is a combination of zinc/zinc oxide.

34. The vehicle of claim 26, wherein said semiconductive organic polymer coating further comprises one or more dyes or pigments.

35. The vehicle of claim 34, wherein said vehicle is an automobile and said one or more external parts are exterior body panels of the automobile body.

* * * * *